US00PP20638P3

(12) United States Plant Patent

Olesen et al.

(10) Patent No.: US PP20,638 P3

(45) Date of Patent: Jan. 12, 2010

(54) *CLEMATIS* PLANT NAMED 'EVIPO039'

(50) Latin Name: *Clematis viticella*
Varietal Denomination: Evipo039

(76) Inventors: Mogens N. Olesen, Kratbjerg 332, Fredensborg (DK) DK-3480; Raymond Evison, Domarie Vineries, Les Sauvagees, St. Sampsons, Guernsey (GB) GY2 4AF ( * ) Notice: Subject to any disclaimer, the term of this patent is extended or adjusted under 35 U.S.C. 154(b) by 57 days.

(21) Appl. No.: 11/998,596

(22) Filed: Nov. 29, 2007

(65) Prior Publication Data

US 2009/0144869 P1 Jun. 4, 2009

(51) Int. Cl.
*A01H 5/00* (2006.01)

(52) U.S. Cl. ..... Plt./228

(58) Field of Classification Search ..... Plt./228
See application file for complete search history.

(56) References Cited

OTHER PUBLICATIONS

Upov Plant Variety Database 2008/05 p. 1.*

Poulsen Roser A/S, CPVO application for plant breeders rights to European Union, Clematis Variety denomination Evipo039, filed Jun. 2, 2006 (7 pages) Denmark.

Poulsen Roser A/S, Invoice marking first date of distribution of claimed plant, dated Aug. 1, 2008, (1 page) Denmark.

Poulsen Roser A/S, screen print from company database, (1 page) Denmark.

* cited by examiner

*Primary Examiner*—Annette H Para

(57) ABSTRACT

A new *Clematis* plant with profuse, light violet flowers and early flowering habit. The variety successfully propagates from softwood cuttings and is suitable for cultivation commercial nursery culture culture. This new and distinct variety has shown to be uniform and stable in the resulting generations from asexual propagation from vegetative cuttings.

2 Drawing Sheets

Botanical classification:
Genus: *Clematis.*
Species: *viticella.*
Variety denomination: 'Evipo039'.

SUMMARY OF THE CLAIMED PLANT

The present discovery constitutes a new and distinct variety of *clematis* plant which was discovered in a cultivated area.

The new *clematis* plant resulted from a naturally occurring mutation of unknown causation on a branch of 'Fairy Blue', U.S. Plant Pat. No. 18,223. The resulting mutation was selected and evaluations were conducted on the resulting *clematis* plants in a controlled environment.

The *clematis* plant of the present discovery is distinguished from the original *clematis* 'Fairy Blue' mainly by differences in the flower center. 'Evipo039' has an arrangement of broad inner tepals at the flower center, while 'Fairy Blue' has a flower center of more narrow, spindly inner tepals.

The objective of the selection of this *clematis* plant was to create a new and distinct variety for nursery culture with unique qualities such as:

1. Profuse light purple flowers with distinct center;
2. Long flowering season;
3. Propagates and flowers more reliably than most double cultivars;
4. Well suited to container nursery culture.

This combination of qualities was lacking in *clematis* plants that were in commercial cultivation and the qualities have been substantially achieved in the new variety.

'Evipo039' was evaluated by Mogens N. Olesen and Raymond J. Evison in their *clematis* development program in the Channel Islands, United Kingdom in 2002. Asexual reproduction of 'Evipo039' by means of vegetative cuttings and traditional layering was first performed by Mogens N. Olesen and Raymond J. Evison in the nursery during the summer of 2002. This initial and subsequent asexual propagations have demonstrated that the characteristics of 'Evipo039' are true to type and are transmitted from one generation to the next.

BRIEF DESCRIPTION OF THE DRAWING

The accompanying color illustrations show as true as is reasonably possible to obtain in color photographs of this type. Observed plants were cultivated for a period of 24 months in 2 liter containers.

DETAILED DESCRIPTION OF THE VARIETY

Figure 1:
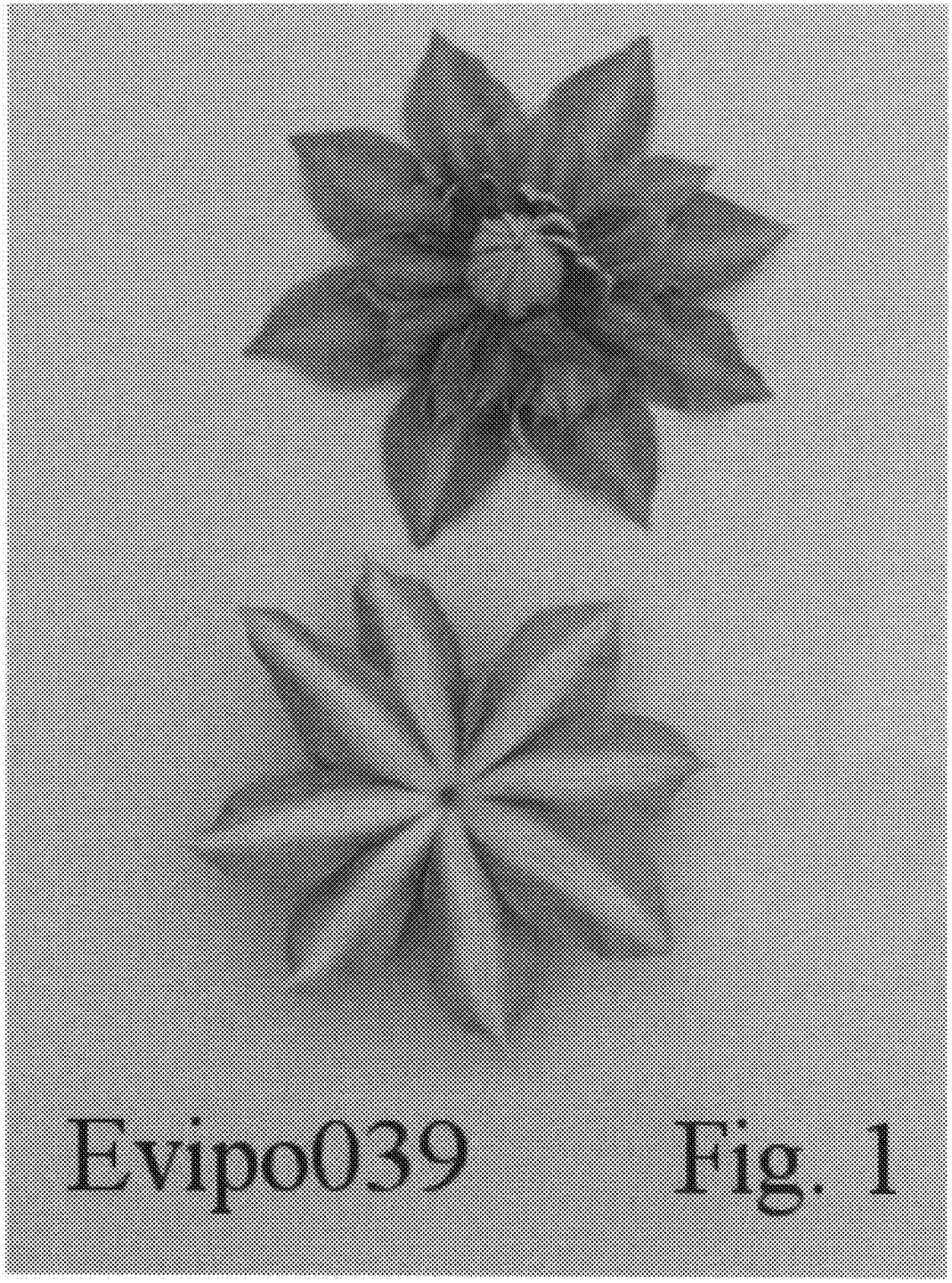
FIG. 1 shows open flowers.
Figure 2:
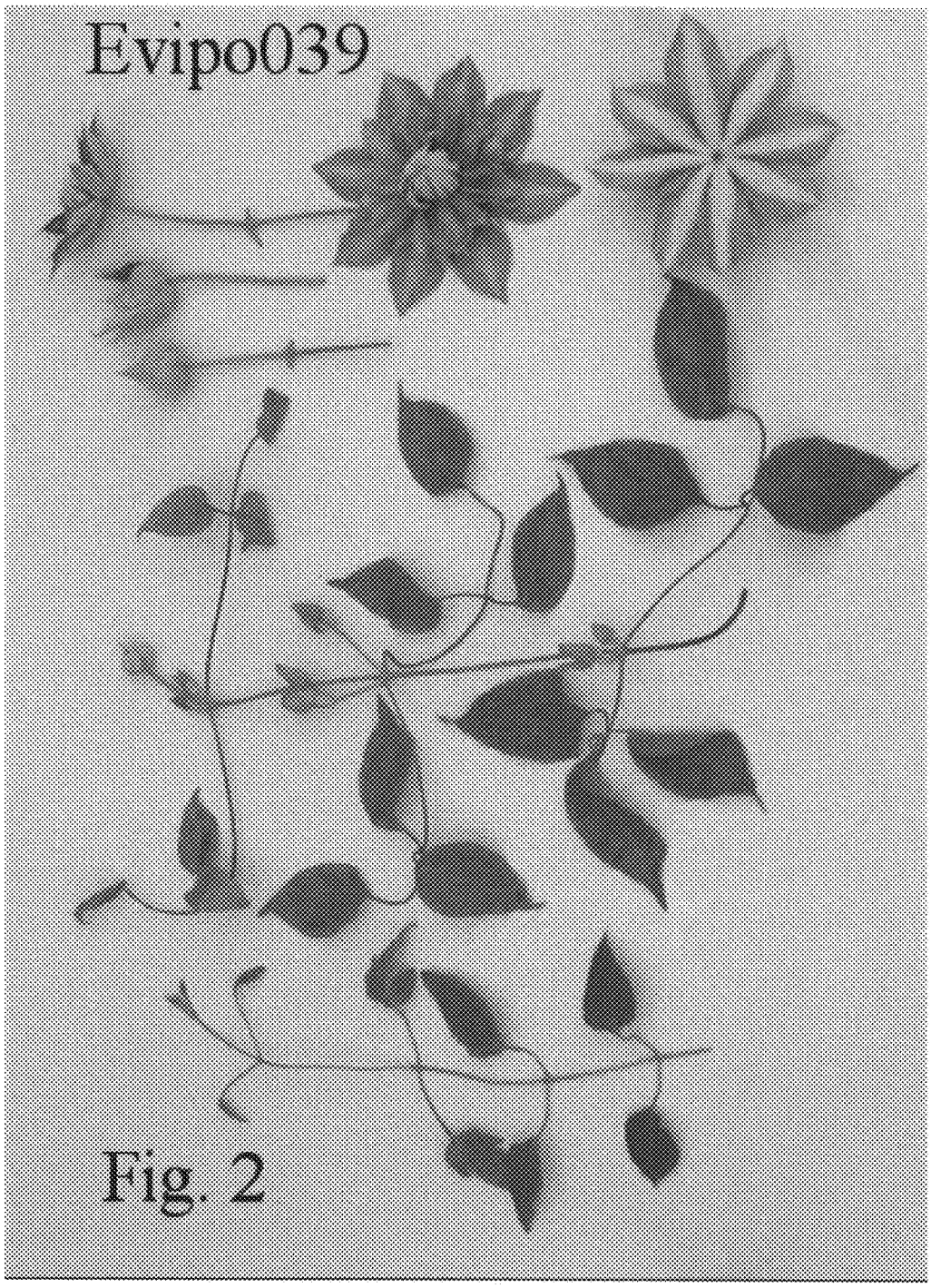
FIG. 2 shows open flowers, flower buds, leaves, and stems.

The following is a detailed description of 'Evipo039', as observed in its growth throughout the flowering period in glasshouses in the Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison two physical characteristics of the *clematis* variety 'Fairy Blue' are compared to 'Evipo039' in Chart 1.

CHART 1

| | 'Evipo039' | 'Fairy Blue' |
|---|---|---|
| Number of petaloid stamens | 250 to 350 | 50 to 100 |
| Dominant tepal color | Violet-Blue Group 92A | Violet Group 87A |

FLOWER AND FLOWER BUD

Blooming habit: Continuous. The natural flowering period is generally from March to November.

Flower bud:

*Size.*—Normally 30 to 50 mm in length. Bud diameter is 20 to 35 mm.

*Bud form.*—Broad based with acute apex. Deltoid.

*Bud color.*—At ¼ opening flower buds are Yellow-Green Group 144B with a margin the color of Yellow-Green Group 149C.

Peduncle:

*Surface texture.*—Smooth and pubescent.

*Length.*—On average 55 to 75 mm.

*Color.*—Typically Green Group 142C.

*Strength.*—Moderately strong.

Receptacle: Absent.

Flower arrangement:

*Location on vine.*—New and old growth.

*Borne.*—On old growth flowers are normally borne singly. On new growth, flowers are borne in compound cymes.

Flower bloom:

*Size.*—On average, flowers are 100 to 190 mm in diameter and 60 to 75 mm in depth.

*Profile.*—Double flowers. Outer tepals extend in single plane. The flower center is globular.

*Fragrance.*—None.

*Lasting quality.*—Flowers normally persist for 10 to 20 days on the plant. As a cut flower, blooms last for an average of 5 days.

Inner tepals:

*Color.*—The inner whorl of tepals are Violet-Blue Group 91A. Intonations of Red-Purple Group become more evident as the flower matures.

*Quantity.*—Normally 250 to 350.

*Size.*—10 to 30 mm in length by 5 to 10 mm wide.

Outer tepals:

*Color.*—Upon opening, the upper and lower surfaces are Violet-Blue Group 92A. The lower surface has a central bar, the color of White Group 155A. After opening, the upper surface is Violet-Blue Group 92A with a midrib the color of Violet-Blue Group 91B. Intonations of Red-Purple Group 70A observed on the midrib, one fourth from the base of the tepal. The lower surface is Violet-Blue Group 92A with a central bar, the color of White Group 155A. Tepals are White Group 155A at the point of attachment.

*Quantity.*—6 to 8.

*Size.*—65 to 100 mm in length by 30 to 45 mm wide.

*Shape.*—Individual tepal shape is ovate to elliptic. The tepal apex is mucronate. The point is extending 3 to 6 mm beyond the curvature of the tepal apex. The tepal base is typically acute.

*Apex recurvature.*—Recurved slightly as flowers mature.

*Tepal cross section.*—Reflexed slightly.

*Margins.*—Entire. Moderate undulations of margin observed.

*Persistence.*—Outer tepals drop off cleanly. The inner whorl of tepals are more persistent.

Reproductive organs: All reproductive flower parts are transformed into tepaloids. Pollen are not formed. There are no anthers, stigmas, or pistils present. No seeds are produced.

PLANT

Plant form: Climbing.

Size: Seasons growth attains 1.2 to 1.5 meters in height. Average spread is 75 cm.

Hardiness: Trials to date show the variety hardy in USDA Zones 4–9.

Stems:

*Color.*—Juvenile stems are generally Greyed-Brown Group 200A. Mature stems are Greyed-Orange Group 175B.

*Internodes.*—On average, 110 to 170 mm cm between nodes. Cylindrical in form.

*Surface.*—Juvenile growth is smooth and pubulent. Mature stems are generally ribbed.

Plant foliage:

*Leaf characteristics.*—Deciduous.

*Arrangement.*—Trifoliate.

*Leaf size.*—Compound leaves are normally 150 to 190 mm (l)×110 to 180 mm (w). Leaflets are normally 60 mm (l)×40 mm (w).

*Abundance.*—Generally, there are 14 leaves per 100 cm of stem.

*Leaf color.*—The upper surfaces of mature leaflets are Green Group 138A while the lower surfaces are Green Group 139D. Upper surfaces of juvenile leaflets are are Green Group 141B while the lower surfaces are Green Group 139C.

*Stipules.*—Absent.

*Petioles.*—Size: Normally 50 to 90 mm in length. Texture: Smooth. Color: Greyed-Purple Group N186C on upper surface. Lower surface is Yellow-Green Group 146D. Clasping: By leaf petiole.

*Petioloule.*—Size: Terminal leaf petioloules are normally 8 to 40 mm in length. Texture: Smooth. Color: Greyed-Purple Group 183B.

*Leaflet shape.*—Generally ovate. The base is rounded. Apex is acute.

*Margin.*—Entire.

*Surface.*—The upper and lower surfaces are smooth.

*Thickness.*—Moderate.

*Glossiness.*—New foliage is glossy. Mature foliage has a matte appearance.

Disease resistance: Subject to any disease that normally attacks the species. However the variety is more tolerant to *clematis* wilt than some *clematis*.

We claim:

1. A new and distinct variety of *clematis* plant named 'Evipo039', substantially as described and illustrated, due to its abundant light violet flowers, vigorous and compact growth, early flowering habit, suitability for commercial nursery container production from soft wood cuttings, durable flowers and foliage which make the variety suitable for distribution in the nursery industry.

* * * * *